United States Patent [19]
Lex

[11] Patent Number: 5,815,279
[45] Date of Patent: Sep. 29, 1998

[54] METHOD AND DEVICE FOR OPTICALLY CHARACTERIZING A SURFACE

[75] Inventor: Konrad Lex, Königsdorf, Germany

[73] Assignee: Byk-Gardner GmbH, Geretsried, Germany

[21] Appl. No.: 679,551

[22] Filed: Jul. 12, 1996

[30] Foreign Application Priority Data

Jul. 13, 1995 [DE] Germany ................ 195 25 566.6

[51] Int. Cl.⁶ ................................................ G01N 21/47
[52] U.S. Cl. ............................................................ 356/446
[58] Field of Search ................... 356/402–411, 445–448, 356/326, 328; 250/226

[56] References Cited

U.S. PATENT DOCUMENTS 4,479,718  10/1984  Alman ....................................... 356/405
5,319,437  6/1994  Van Aken et al. ....................... 356/328

FOREIGN PATENT DOCUMENTS 2151353  7/1985  United Kingdom ................... 356/407

OTHER PUBLICATIONS

Egan et al, "Retroreflectance Measurements . . . Coatings" Applied Optics vol. 15 No. 7 pp. 1845–1849, Jul. 1976.

Primary Examiner—K. Hantis
Attorney, Agent, or Firm—Ohlandt, Greeley, Ruggiero & Perle

[57] ABSTRACT

In a method and a device for optically characterizing a goniochromatic surface, for example a metallic painting surface, only a fixed measuring angle setting is used according to the invention.

25 Claims, 1 Drawing Sheet

METHOD AND DEVICE FOR OPTICALLY CHARACTERIZING A SURFACE

This invention relates to a method and device for optically characterizing a surface and in particular a goniochromatic surface.

BACKGROUND OF THE INVENTION

A surface is called goniochromatic, if optical measuring quantities, such as its color values, clearly depend on the illumination angle of the light to be reflected and on the measuring angle or observation angle of the reflected light when performing a reflection measurement. Such surfaces may be metallic paint surfaces or lustrous paint surfaces (interference color surfaces) or other surfaces exhibiting corresponding effects, particularly synthetic material surfaces having embedded metal particles or transparent particles.

In the following the term optical descriptors will be used which shall characterize optical measuring quantities, such as color values (tristimulus values), brightness, hue, degree of saturation or purity, and magnitudes, such as reflection factors, which are convertable into such measuring quantities, respectively.

Goniochromatic surfaces are used in many fields in industry and handycraft, for example in metallic or lustrous paints in the automobile industry, particularly under the view points of designs. Equally, also many synthetic material products have surfaces exhibiting a metallic effect. Such surfaces must be characterized at the time of manufacturing or repair in order to provide a documentation, which is as objective as possible, and in order to also enable a comparison with a predetermined standard, which is as objective as possible. In this case there is often need of the naturally subjectively influenced visionary judgement of well skilled and experienced and accordingly highly payed qualified persons. Conventional objective-physical characterizing methods and devices are complicated, time consuming and accordingly costly.

Until now the skilled persons have been of the opinion that for a reasonable characterization of such goniochromatic surfaces at least three measurements under different angles are required. In U.S. Pat. No. 4,479,718 three measurements under 15°, 45° and 110°, respectively, between the measuring device and the direction of the light beam reflected in accordance with the classic reflection law with respect to the goniochromatic surface, for example, are used. In order to perform a color characterize, these measurements have to be conducted using different light wavelengths.

From the strong curvature of the hue-versus-angle curves it is concluded that these curves have to be described using a polynomial of at least second order which generally includes three parameters. In accordance with the technical teaching of the cited patent document, these three parameters have to be determined performing three measurements under different angles and are required for a sufficiently accurate characterization of the goniochromatic surface. Equally, this applies to the angle dependent curves of different descriptors.

It is the technical problem of the present invention to provide a method and a device which enables a simple, practical and nonetheless sufficiently accurate optical characterization of goniochromatic surfaces, in particular.

SUMMARY OF THE INVENTION

This technical problem is solved by providing a method for optically characterizing a goniochromatic surface by measuring optical descriptors, wherein the goniochromatic surface is illuminated by means of an illumination means in an illumination direction and a fraction of the light reflected from the surface is detected using a detector means in the measuring means, characterized in that the characterization is carried out by the measurement under only a single illumination angle between the illumination direction and the surface and under only a single measuring angle between the measuring direction and the surface, and by providing a device for optically characterizing a surface according to a method according to one of the preceeding claims, characterizing that the illumination means is fixed to the illumination angle and the detector means is fixed to the measuring angle.

The invention is based on the surprising finding that an optical characterization under only a single angle adjustment of the illumination means, the detector means and the goniochromatic surfaces is sufficient for practical needs, such as for the quality assurance of a painting means. In contrast to the up to date opinion of the skilled persons and particularly in contrast to the technical teaching of the cited U.S. patent document the inventive method and the inventive device, respectively, achieve a sufficient accuracy for practical applications.

In contrast to the findings of the U.S. Pat. No. 4,479,718 the three parameters of a polynomial of second order in the angle measured of the reflected light beam observed there do not forcibly have to correspond three independent variables, i.e. three degrees of freedom. Regarding a practically sufficient accuracy, it may be assumed that all three parameters have a certain functional relation. This especially applies for applications with surface layers, particularly paints, which exhibit the same or a similar chemical and physical characteristic. For practical requirements it suffices to take into account a single measuring value determined by using the inventive device in accordance with the inventive method for characterizing and comparing a goniochromatic sample surface.

According to a preferred embodiment the illumination means or the detector means includes a color filter for color specific measurements. Thus, the mentioned color values may be determined. Preferably a goniochromatic surface is totally characterized by performing two color specific measurements and one brightness measurement.

To improve the measurement accuracy the illumination means or the detector means may comprise a heat protection filter. This also helps to protect a heat sensitive goniochromatic surface, if the heat protection filter is arranged in the illumination means.

Preferably the measuring angle is different from the illumination angle so that the detector means measures outside the beam reflected from the goniochromatic surface according to the classical reflection law. For better comparability with conventional measuring methods it is advantageous, if the illumination angle amounts to approximately 45°. Preferably the measuring angle ranges between the illumination angle and 90°. As a particularly suited measuring angle the angle of approximately 65° has been found.

As an advantageous measuring angle range for the detector means an angle range about the central measuring angle having an aperture angle of 6° has been found. As an advantageous illumination angle range for the illumination means an angle range about the central illumination angle having an aperture angle of approximately 3° has been found.

For goniochromatic surfaces with embedded metal or interference plates for example in metallic paint or lustrous paint surfaces, because of the finite size of this plate it is useful to illuminate and to measure an extended area on the surface to be measured in order to obtain a useful average formation already for a single measurement. Especially in this case it is very important to homogeneously illuminate this area. Preferably a lamp in the illumination means can illuminate a diffusely scattering surface of an optical element such as of an scattering mat lighting, in order to form an image of the illuminated surface on the surface to be measured.

For particular cases of application it may be useful to compare not only measuring values of different surfaces obtained by the inventive method and the inventive device, respectively, but also to relate the measuring values obtained according to the invention to conventionally obtained measuring values, such as the ones obtained by three angle adjustments mentioned above. To this purpose it may be advantageous to calculate a polynomial of at least second order in the outlet angle of a reflected light beam resulting from the inventive measurement for comparing it with such angle resolved measurements. This method step quasi resembles a calibration on the conventional representation of the measuring values as polynomial parameters.

As already mentioned above, the problem of the measurement of goniochromatic surfaces often arises for painting surfaces, particularly metallic or lustrous painting surfaces. Here a particularly important and advantageous application of this invention resides. Particularly this regards the field of the automobile industry and the automobile workshops. Accordingly a substantial field of application resides in surfaces of automobile bodies.

From the foregoing it becomes readily apparent that the invention is not only related to a method but also to a device for optically characterizing a goniochromatic surface. Accordingly the above mentioned preferred embodiments are to be understood both with respect to the inventive method and with respect to the device according to the invention. Particularly for the inventive device this leads to the result that the illumination means is fixed to the illumination angle and the detector means is fixed to the measuring angle. Accordingly the device is very simple, compact and unexpensively constructable.

According to a particularly simple and robust embodiment the illumination means and the detector means are incorporated in respective receptacles of a block forming a device body, preferably a metal block, the receptacles defining the illumination angles and the measuring angle, respectively. The block may practically have an annex for the goniochromatic surface to be measured.

If a limitation to a certain illumination angle (range) and measuring angle (range), respectively, is desired, then the illumination means and the detector means, respectively, may include corresponding apertures.

According to a simple and preferred embodiment the detector means measures the reflected light using a photoelement.

Since the inventive device may be compactly and simply constructed for the reasons mentioned above and the arrangement of the illumination means and the detector means in a massive block leads to a huge robustness, at least a part containing the illumination means and the detector means, for example the mentioned block, may be embodied as movable and applicable to a surface to be measured per hand.

Other advantages, features and application possibilities of the present invention may be obtained from the following description of embodiments in connection with the drawings. Therein the single figure schematically illustrates a cross section across an embodiment of an inventive device.

DESCRIPTION OF THE PREFERRED EMBODIMENTS

Figure 1:
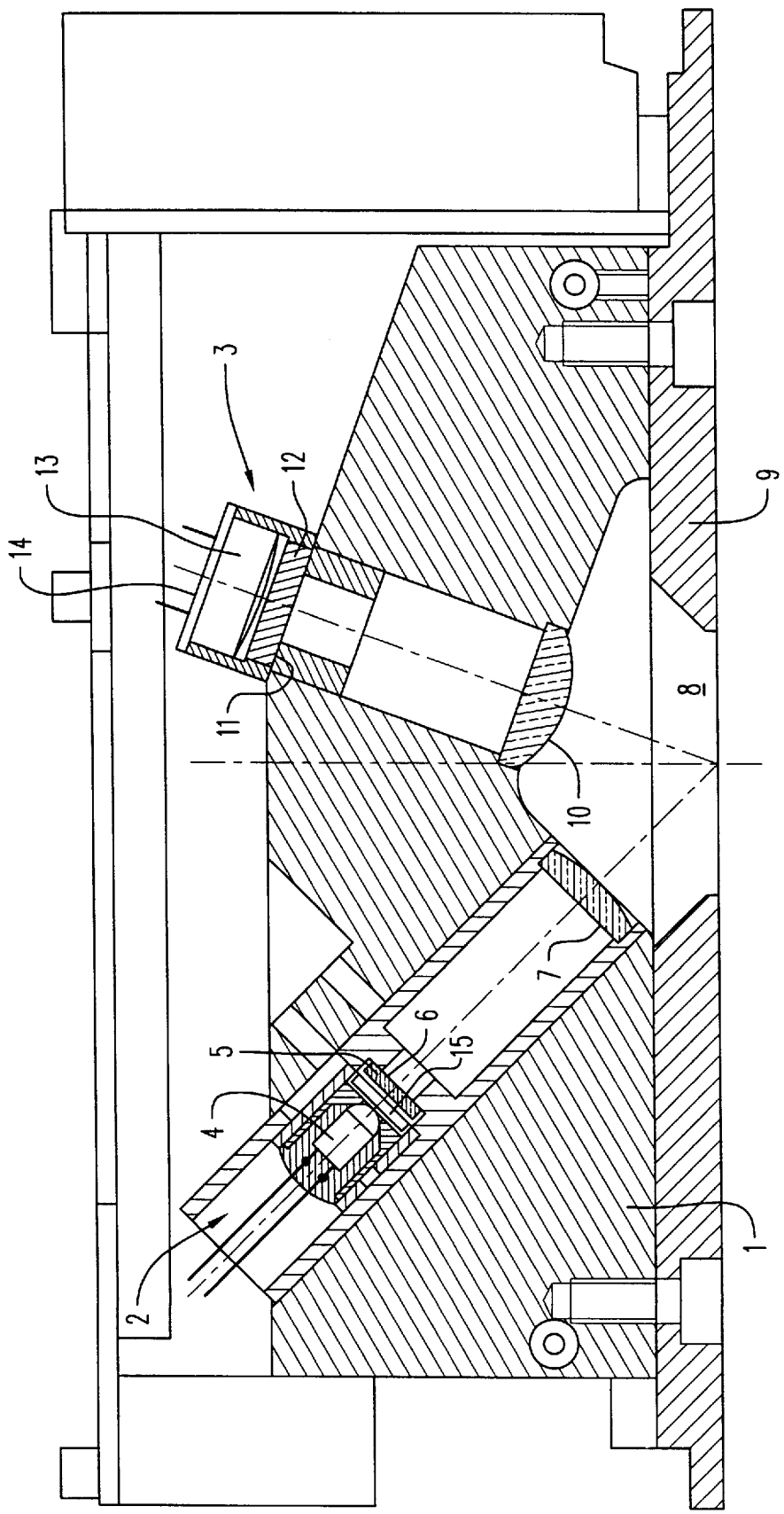

FIG. 1 shows a block 1 having an illumination means 2 inserted in a receptacle in the block and detector means 3 inserted in another receptacle in the block. The illumination means 2 includes a lamp 4, a scattering mat lighting 5 illuminated by the lamp, and an aperture 6 arranged at the mat lighting on the side opposite to the lamp. The illumination means may include a color filter or a heat filter 15. The light passed by the aperture 6 is bundled by means of a collecting lens 7 and illuminates the goniochromatic surface to be measured.

To this purpose the illuminated area of the goniochromatic surface is arranged in a section 8 in an annex 9, by bringing the surface to be measured and the annex 9 in face contact with each other.

In the shown embodiment the annex 9 is provided at a plate which is attached to the block 1 via screws in a releasable fashion. Thus, the plate may easily be exchanged if it gets damaged or contaminated or it should be replaced by an alternatively designed plate for a particular application.

The illumination angle between the optical axis of the illumination means 2 and the surface to be measured amounts to 45°. The optical axis of the detector means 3 forms an angle of 70° with respect to the surface to be measured. The detector means 3 exhibits a collecting lens 10 at its side directed to the surface to be measured which bundles light reflected from the goniochromatic surface in the direction of an aperture 11, behind which a heat protection filter 12 is located. Behind this filter another lens 13 is provided through which the light impinges onto a photoelement 14.

All together the illumination means 2 and the detector means 3 are constructed such that the illumination angle range provides an aperture angle of 3° and the measuring angle range provides an aperture angle of 6°.

The illumination means 2 is located in a piece of pipe which after releasing a securing thread stud bold may be easily drawn in the upward direction from the receptacle in the block 1. Moreover the lamp 4 is accessible from behind without disassembling the piece of pipe and can be drawn out after releasing another securing thread stud bold, if it has to be replaced, for example.

The detector means 3 is accomodated in a second piece of pipe having an outer shoulder which is inserted in the corresponding receptacle in the frame 1 up to an end stop of the outer shoulder at a frame outer surface, except for a collecting lens 10 glued in the frame 1. Also this piece of pipe may accordingly be easily detached to the outer side.

Moreover the block 1 having the illumination means 2 and the detector means 3 is surrounded by a housing and frame construction which is only briefly indicated in the drawing. This housing construction also includes a control and analysis electronics which controls a display means not shown, namely an electronic display, arranged at the side opposite to the surface to be measured of the device outside the housing. The total device has a power supply in form of a battery which is also integrated in the housing, so that it can independently of a network be operated and moved as a hand device.

I claim:

1. A method for optically characterizing a goniochromatic surface by measuring optical descriptors, the method comprising the steps of:

illuminating the goniochromatic surface by means of an illumination means in an illumination direction; and measuring a fraction of light reflected from the goniochromatic surface by using a detector means so as to determine the optical descriptors for characterizing the goniochromatic surface, wherein the fraction of light is measured under only a single illumination angle between the illumination direction and the goniochromatic surface and under only a single measuring angle between the detector means and the goniochromatic surface.

2. The method according to claim 1, wherein the optical descriptors include a brightness measurement for characterizing the goniochromatic surface.

3. The method according to claim 1, wherein the illumination means includes color filter means for enabling color specific measurement.

4. The method according to claim 3, wherein the optical descriptors include two color specific measurements and one brightness measurement for characterizing the goniochromatic surface.

5. The method according to claim 1, wherein the illumination means and/or the detector means includes a heat protection filter.

6. The method according to claim 1, wherein the measuring angle is different from the illumination angle.

7. The method according to claim 1, wherein the illumination angle is 45°.

8. The method according to claim 1, wherein the measuring angle is 90° or ranges between the illumination angle and 90°.

9. The method according to claim 1, wherein the measuring angle ranges between 60° and 70°.

10. The method according to claim 1, wherein the detector means monitors a measuring angle range around the measuring angle of the detector means having an aperture angle less than 15°.

11. The method according to claim 1, wherein the illumination means illuminates at an illumination angle range around the illumination angle of the illumination means having an aperture angle smaller than 10°.

12. The method according to claim 1, wherein a lamp in the illumination means illuminates a diffusely scattering surface of an optical element.

13. The method according to claim 1, further including the step of calculating a polynomial of at least second order in the measuring angle of the fraction of light reflected from the goniochromatic surface, the polynomial being compared with angle resolved measurements.

14. The method according to claim 1, wherein the goniochromatic surface is a painting surface.

15. The method according to claim 14, wherein the goniochromatic surface is a painting surface of an automobile body.

16. A device for optically characterizing the goniochromatic surface according to the method of claim 1, wherein the illumination means is fixed at the illumination angle and the detector means is fixed at the measuring angle.

17. The device according to claim 16, wherein the illumination means and the detector means are incorporated in respective receptacles defining the illumination angle and the measuring angle, respectively, in a block forming a body of the device.

18. The device according to claim 16, wherein a block is provided with an annex for the goniochromatic surface.

19. The device according to claim 16, wherein the illumination means and/or the detector means include an aperture defining an illumination angle range and a measuring angle range, respectively.

20. The device according to claim 16, wherein the detector means comprises at least one photoelement.

21. The device according to claim 16, wherein at least a part of the device including at least the illumination means and the detector means may be moved and placed onto the goniochromatic surface.

22. The device according to claim 21, further comprising a display and a user control means.

23. The method according to claim 7, wherein the measuring angle is 90° or ranges between the illumination angle and 90°.

24. The device according to claim 17, wherein the illumination means and/or the detector means include an aperture defining an illumination angle range of the illumination angle and a measuring angle range of the measuring angle, respectively.

25. The device according to claim 18, wherein the illumination means and/or the detector means include aperture defining an illumination angle range and a measuring angle range, respectively.

* * * * *